(12) United States Patent
Nichols

(10) Patent No.: US 9,823,259 B1
(45) Date of Patent: Nov. 21, 2017

(54) DETECTION DEVICE FOR CANNABINOID USE

(71) Applicant: Walter Nichols, St. Joseph, MO (US)

(72) Inventor: Walter Nichols, St. Joseph, MO (US)

( * ) Notice: Subject to any disclaimer, the term of this patent is extended or adjusted under 35 U.S.C. 154(b) by 41 days.

(21) Appl. No.: 15/094,380

(22) Filed: Apr. 8, 2016

(51) Int. Cl.

| | |
|---|---|
| *G01N 33/94* | (2006.01) |
| *G01N 1/10* | (2006.01) |
| *G01N 33/48* | (2006.01) |
| *A61B 5/15* | (2006.01) |
| *G01N 21/75* | (2006.01) |
| *A61B 10/00* | (2006.01) |
| *G01N 33/487* | (2006.01) |
| *G01N 31/22* | (2006.01) |
| *G01N 21/01* | (2006.01) |
| *G01N 25/48* | (2006.01) |
| *C12Q 1/68* | (2006.01) |
| *A61B 5/157* | (2006.01) |

(52) U.S. Cl.
CPC ....... *G01N 33/948* (2013.01); *A61B 10/0045* (2013.01); *A61B 10/0096* (2013.01); *G01N 21/75* (2013.01); *G01N 33/4875* (2013.01); *A61B 5/157* (2013.01); *A61B 5/150435* (2013.01); *A61B 5/150511* (2013.01); *C12Q 1/6816* (2013.01); *G01N 25/4813* (2013.01); *G01N 31/22* (2013.01); *G01N 2201/0228* (2013.01); *Y10S 436/901* (2013.01)

(58) Field of Classification Search
CPC ............ C12Q 2565/607; C12Q 1/6816; G01N 21/8483; G01N 33/948; G01N 15/0205; G01N 21/75; G01N 2201/0228; G01N 25/4813; G01N 31/22; G01N 33/4875; A61B 10/0045; A61B 10/0096; A61B 5/150435; A61B 5/150511; A61B 5/157; Y10S 436/901

See application file for complete search history.

(56) References Cited

U.S. PATENT DOCUMENTS

| | | | |
|---|---|---|---|
| 4,995,402 A | * | 2/1991 | Smith .................... A61B 5/157 206/569 |
| 7,749,772 B1 | | 7/2010 | Wang |
| 7,977,107 B2 | | 7/2011 | Day et al. |
| 8,518,653 B2 | | 8/2013 | Takkinen et al. |
| 2004/0082878 A1 | * | 4/2004 | Baldwin ............ A61B 10/0051 600/573 |

\* cited by examiner

*Primary Examiner* — Jennifer Wecker
(74) *Attorney, Agent, or Firm* — Stevenson IP, LLC

(57) ABSTRACT

A detection device for cannabinoid use including a base unit and a display screen disposed on the base unit. A central processing unit and a tetrahydrocannabinol testing device are disposed within the base unit. A testing slot is disposed on a bottom portion of the base unit, with a back end of the testing slot disposed within the tetrahydrocannabinol testing device. Each of a plurality of testing strips is slidably and removably disposed within the testing slot. A printer has a pair of T-shaped attachment extensions. Each of the pair of attachment extensions and a universal serial bus plug disposed on the printer simultaneously removably and slidably engages each of a pair of attachment slots and a universal serial bus port disposed on the base unit, respectively. The tetrahydrocannabinol testing device is configured to analyze and calculate the presence and amount of tetrahydrocannabinol in a person's bloodstream.

4 Claims, 5 Drawing Sheets

DETECTION DEVICE FOR CANNABINOID USE

BACKGROUND OF THE INVENTION

Various types of analyte detection devices are known in the prior art. However, what has been needed is a detection device for cannabinoid use including a base unit and a display screen disposed on the base unit. What has been further needed is a central processing unit disposed within the base unit, a tetrahydrocannabinol testing device disposed within the base unit, and a testing slot disposed on a bottom portion of the base unit. Each of a plurality of testing strips is slidably and removably disposed within the testing slot, with a back end of the testing slot disposed within the tetrahydrocannabinol testing device. The tetrahydrocannabinol testing device is configured to analyze and calculate the presence and amount of tetrahydrocannabinol in a person's bloodstream. Lastly, what has been needed is a printer removably attachable to the base unit. The detection device for cannabinoid use thus allows a user to test and calculate the presence and amount of tetrahydrocannabinol in the person's bloodstream using the smallest amount of bodily fluid possible. This detection device further eliminates the need of the user to transport the person to a hospital or laboratory testing facility to test for tetrahydrocannabinol, a visit which often requires that the user wait days or even months for the test results. The testing device will also provide a more accurate calculation of the amount of tetrahydrocannabinol in the person's bloodstream, since both the testing and the results of the testing will be completed in a matter of minutes. This detection device is ideal for use by law enforcement officials who must rapidly detect and analyze the presence of tetrahydrocannabinol in the person's bloodstream in order to better protect the public's welfare.

FIELD OF THE INVENTION

The present invention relates to analyte detection devices, and more particularly, to a detection device for cannabinoid use.

SUMMARY OF THE INVENTION

The general purpose of the present detection device for cannabinoid use, described subsequently in greater detail, is to provide a detection device for cannabinoid use which has many novel features that result in a detection device for cannabinoid use which is not anticipated, rendered obvious, suggested, or even implied by prior art, either alone or in combination thereof.

To accomplish this, the present detection device for cannabinoid use includes a substantially trapezoidal handheld portable base unit having a convexly curved bottom portion, a linear top edge, a right side, a left side, a front side, and an exterior surface. A display screen is disposed on the front side of the base unit proximal the top edge. An antimicrobial covering is disposed on the exterior surface of the base unit. A first battery compartment is disposed within the base unit, and a pair of rechargeable batteries is disposed within the first battery compartment. A central processing unit and a tetrahydrocannabinol testing device are also disposed within the base unit. A testing slot has a front end medially disposed on the bottom portion of the base unit and a back end disposed within the tetrahydrocannabinol testing device.

The detection device for cannabinoid use further includes a plurality of elongated rectangular sterile testing strips, with each of the plurality of testing strips slidably and removably disposed within the testing slot. The plurality of testing strips is optionally a pair of a plurality of testing strips including a first pair and a second pair. Each of the plurality of testing strips of the first pair is configured to receive a sample of blood and each of the plurality of testing strips of the second pair is configured to receive a sample of saliva. A length of each of the plurality of testing strips of the first pair is shorter than a length of each of the plurality of testing strips of the second pair in order to better ensure that the test strips receiving the sample of saliva are long enough to reach into a person's mouth.

A testing activation control is disposed on the front side of the base unit proximal the bottom portion. Each of a right attachment slot and a left attachment slot of a pair of T-shaped attachment slots is disposed within the top edge of the base unit proximal the right side and the left side, respectively. A universal serial bus port is medially disposed within the top edge of the base unit between the right attachment slot and the left attachment slot.

A handheld portable printer has a linear bottom surface, a back surface, a right surface, a left surface, a universal serial bus plug substantially medially disposed on the bottom surface, and a pair of T-shaped attachment extensions including a right attachment extension and a left attachment extension. Each of the right attachment extension and the left attachment extension is disposed on the bottom surface proximal the right surface and the left surface, respectively. A second battery compartment is disposed within the portable printer, with a rechargeable battery disposed within the second battery compartment. A distance between the right attachment slot and the left attachment slot is equal to a distance between the right attachment extension and the left attachment extension. Each of the right attachment extension, the left attachment extension, and the universal serial bus plug simultaneously removably and slidably engages the right attachment slot, the left attachment slot, and the universal serial bus port, respectively.

The detection device for cannabinoid use optionally includes a pair of substantially rectangular rubberized gripping members. The gripping members include a right gripping member and a left gripping member. Each of the right gripping member and the left gripping member is disposed on the right side of the base unit and the left side of the base unit, respectively. The pair of gripping members allows a user to maintain the proper grip on the base unit.

The tetrahydrocannabinol testing device is configured to analyze and calculate, using previously known detection methods, the presence and amount, in nanograms per milliliter, of tetrahydrocannabinol in the person's bloodstream when one of the plurality of testing strips containing a sample of one of the person's saliva and blood is disposed within the testing slot and the testing activation control is depressed by a user. It is also envisioned that the base unit can be structured to analyze body samples and test for other drugs including, but not limited to, cocaine, methamphetamine, and alcohol. The display screen is configured to display the presence and amount of tetrahydrocannabinol in the person's bloodstream as calculated by the tetrahydrocannabinol testing device. The printer is configured to print a receipt showing the presence and amount of tetrahydrocannabinol in the person's bloodstream as calculated by the tetrahydrocannabinol testing device. The display screen, the pair of rechargeable batteries, the central processing unit, the tetrahydrocannabinol testing device, the testing activation control, the printer, and the rechargeable battery are in operational communication with each other.

Thus has been broadly outlined the more important features of the present detection device for cannabinoid use so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
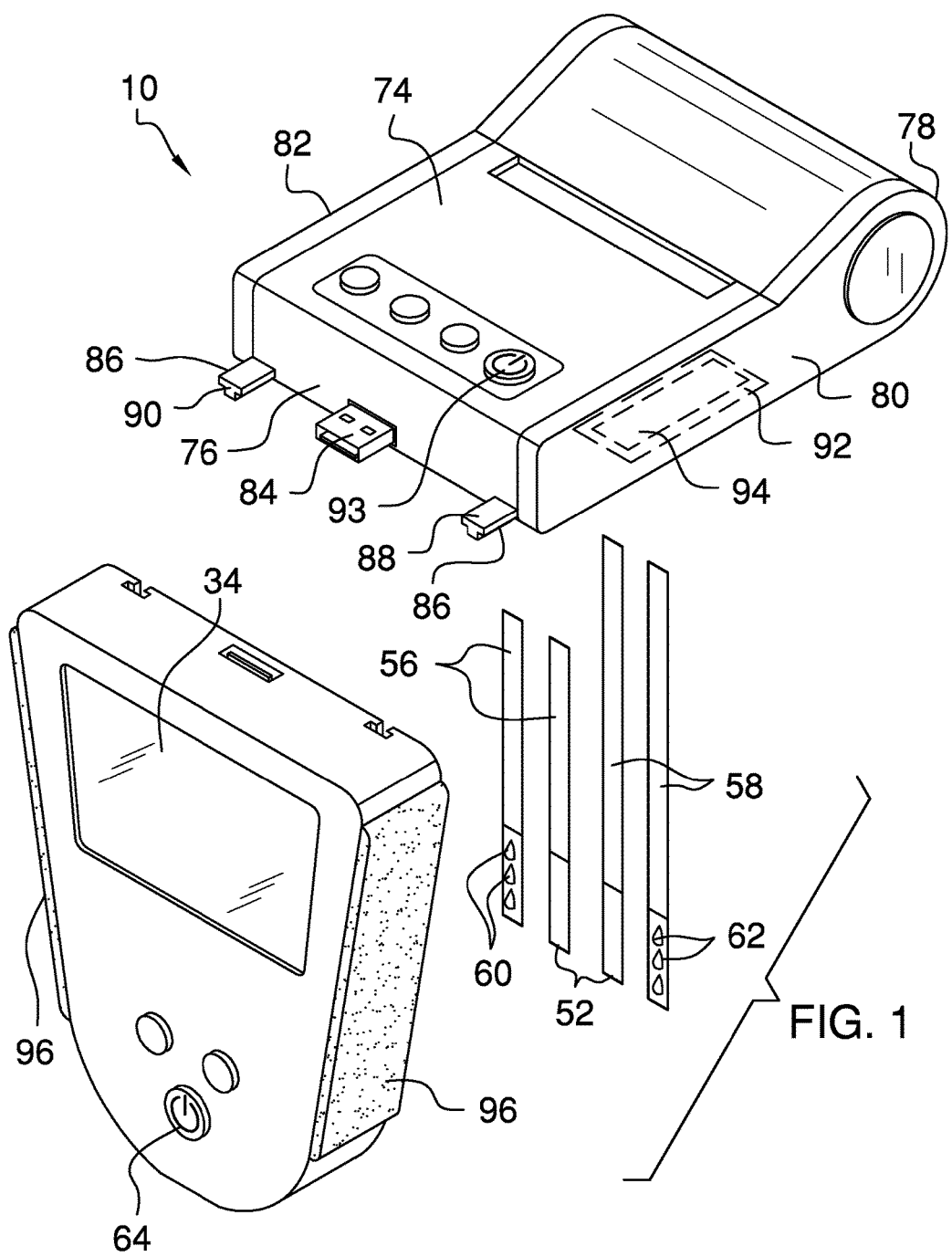
FIG. 1 is an exploded view.
Figure 2:
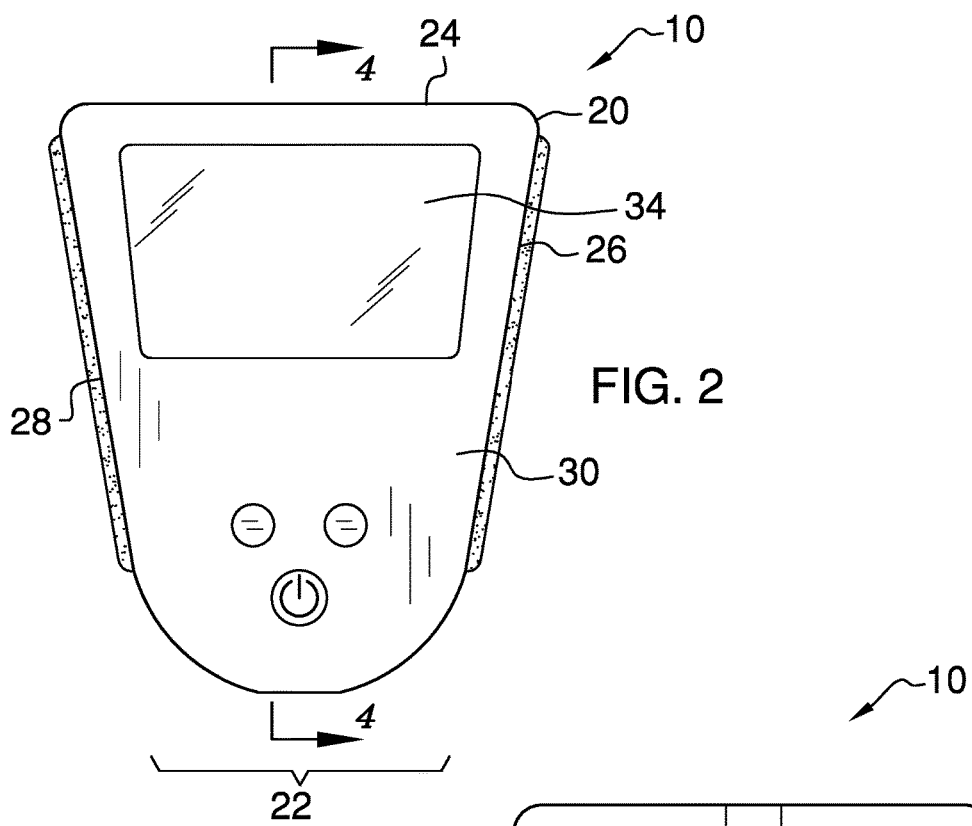
FIG. 2 is a front elevation view showing a base unit.
Figure 3:
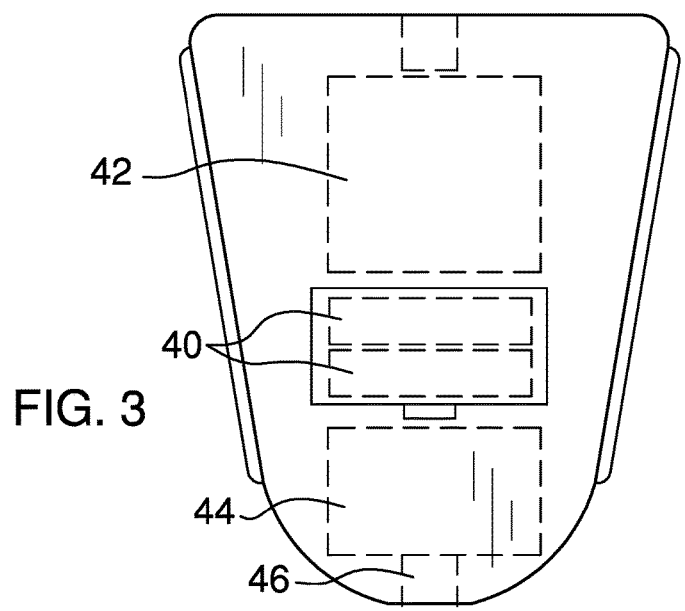
FIG. 3 is a rear elevation view showing the base unit.
Figure 4:
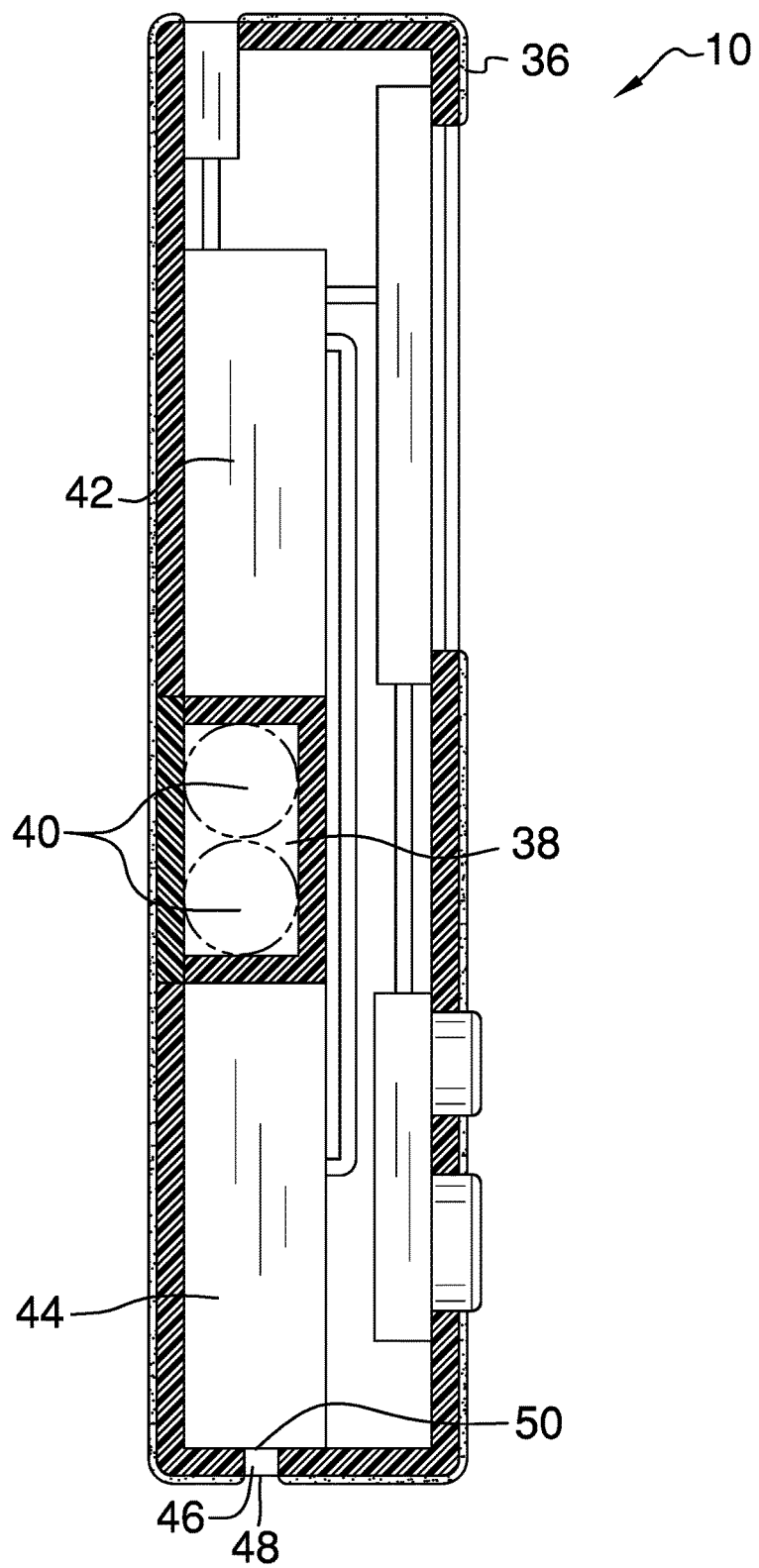
FIG. 4 is a cross-sectional view taken along line 4-4 of FIG. 2.
Figure 5:
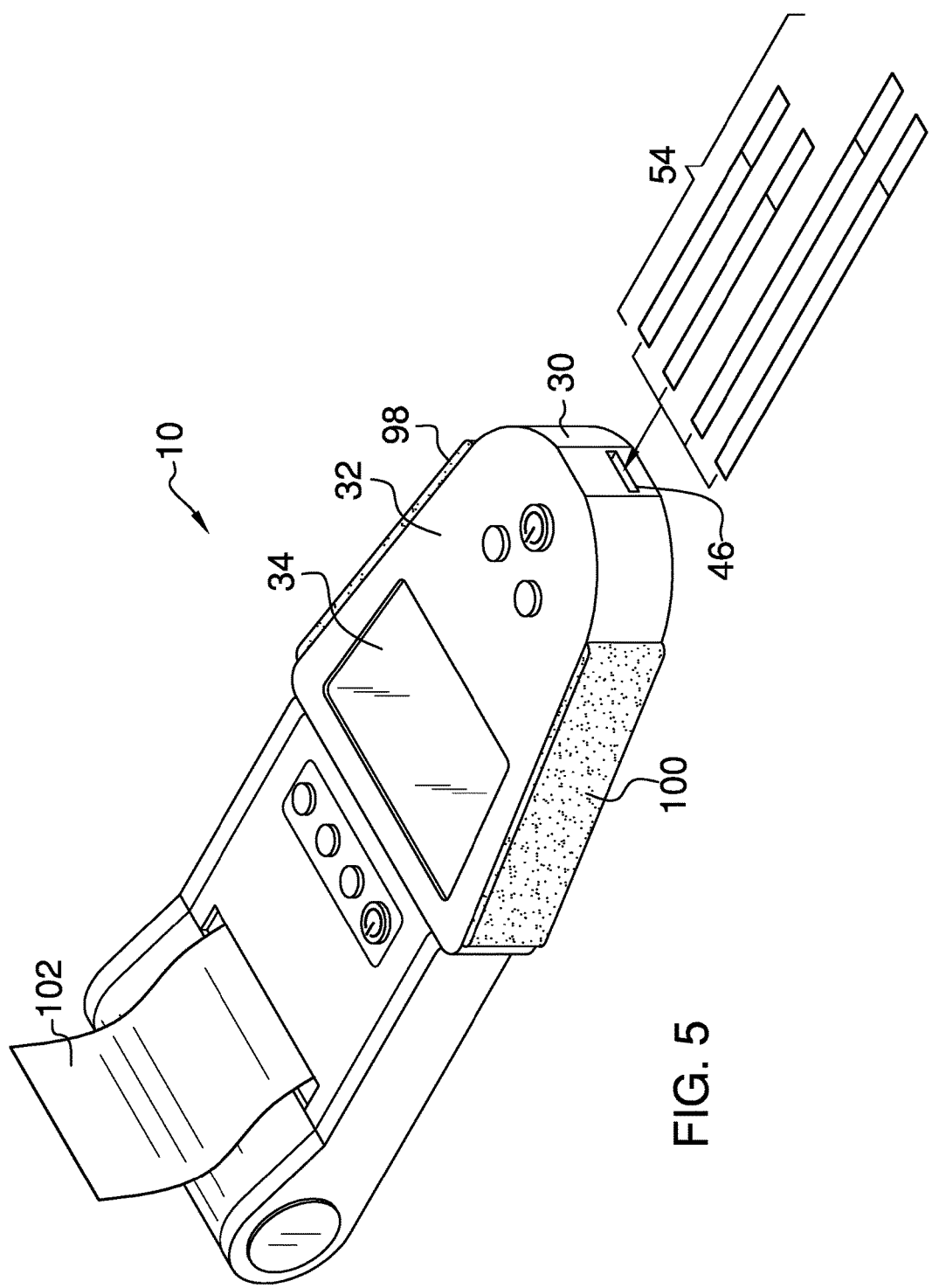
FIG. 5 is an isometric view.
Figure 6:
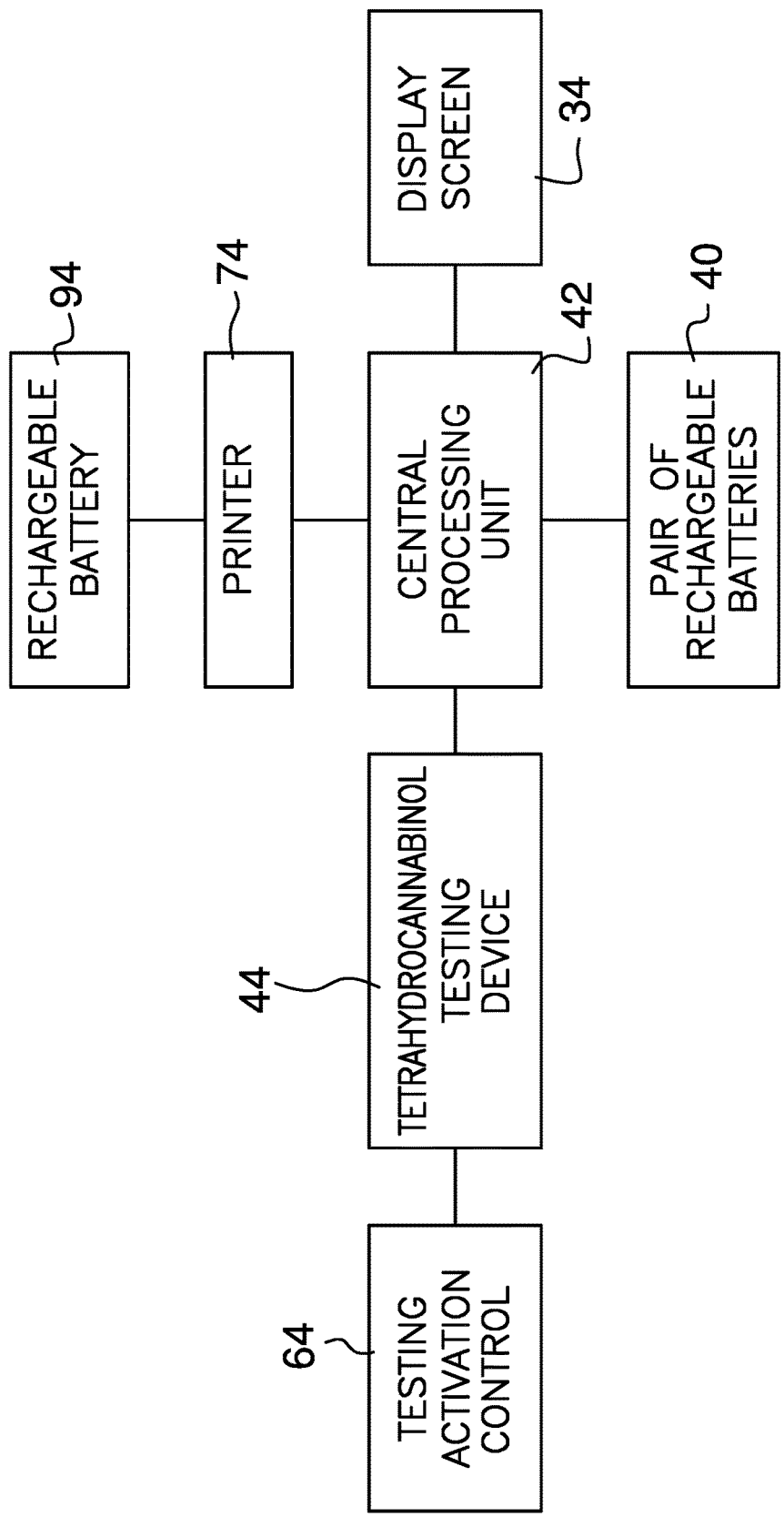
FIG. 6 is a block diagram.

With reference now to the drawings, and in particular FIGS. 1 through 6 thereof, an example of the instant detection device for cannabinoid use employing the principles and concepts of the present detection device for cannabinoid use and generally designated by the reference number 10 will be described.

Referring to FIGS. 1 through 6 the present detection device for cannabinoid use 10 is illustrated. The detection device for cannabinoid use 10 includes a substantially trapezoidal handheld portable base unit 20 having a convexly curved bottom portion 22, a linear top edge 24, a right side 26, a left side 28, a front side 30, and an exterior surface 32. A display screen 34 is disposed on the front side 30 of the base unit 20 proximal the top edge 24. An antimicrobial covering 36 is disposed on the exterior surface 32 of the base unit 20. A first battery compartment 38 is disposed within the base unit 20, and a pair of rechargeable batteries 40 is disposed within the first battery compartment 38. A central processing unit 42 and a tetrahydrocannabinol testing device 44 are also disposed within the base unit 20. A testing slot 46 has a front end 48 medially disposed on the bottom portion 22 of the base unit 20 and a back end 50 disposed within the tetrahydrocannabinol testing device 44.

The detection device for cannabinoid use 10 further includes a plurality of elongated rectangular sterile testing strips 52, with each of the plurality of testing strips 52 slidably and removably disposed within the testing slot 46. The plurality of testing strips 52 is optionally a pair of a plurality of testing strips 54 including a first pair 56 and a second pair 58. Each of the plurality of testing strips of the first pair 56 is configured to receive a sample of blood 60 and each of the plurality of testing strips of the second pair 58 is configured to receive a sample of saliva 62. A length of each of the plurality of testing strips of the first pair 56 is shorter than a length of each of the plurality of testing strips of the second pair 58.

A testing activation control 64 is disposed on the front side 30 of the base unit 20 proximal the bottom portion 22. Each of a right attachment slot 66 and a left attachment slot 68 of a pair of T-shaped attachment slots 70 is disposed within the top edge 24 of the base unit 20 proximal the right side 26 and the left side 28, respectively. A universal serial bus port 72 is medially disposed within the top edge 24 of the base unit 20 between the right attachment slot 66 and the left attachment slot 68.

A handheld portable printer 74 has a linear bottom surface 76, a back surface 78, a right surface 80, a left surface 82, a universal serial bus plug 84 substantially medially disposed on the bottom surface 76, and a pair of T-shaped attachment extensions 86 including a right attachment extension 88 and a left attachment extension 90. Each of the right attachment extension 88 and the left attachment extension 90 is disposed on the bottom surface 76 proximal the right surface 80 and the left surface 82, respectively. A second battery compartment 92 is disposed within the portable printer 74, with a rechargeable battery 94 disposed within the second battery compartment 92. A printer activation control 93 is disposed on the printer 74. A distance between the right attachment slot 66 and the left attachment slot 68 is equal to a distance between the right attachment extension 88 and the left attachment extension 90. Each of the right attachment extension 88, the left attachment extension 90, and the universal serial bus plug 84 simultaneously removably and slidably engages the right attachment slot 66, the left attachment slot 68, and the universal serial bus port 72, respectively.

The detection device for cannabinoid use 10 optionally includes a pair of substantially rectangular rubberized gripping members 96. The pair of gripping members 96 include a right gripping member 98 and a left gripping member 100. Each of the right gripping member 98 and the left gripping member 100 is disposed on the right side 26 of the base unit 20 and the left side 28 of the base unit 20, respectively.

The tetrahydrocannabinol testing device 44 is configured to analyze and calculate, using previously known detection methods, the presence and amount of tetrahydrocannabinol in the person's bloodstream when one of the plurality of testing strips 52 containing a sample of one of the person's saliva and blood is disposed within the testing slot 46 and the testing activation control 64 is depressed by a user. The display screen 34 is configured to display the presence and amount of tetrahydrocannabinol in the person's bloodstream as calculated by the tetrahydrocannabinol testing device 44. The printer 74 is configured to print a receipt 102 showing the presence and amount of tetrahydrocannabinol in the person's bloodstream as calculated by the tetrahydrocannabinol testing device 44. The display screen 34, the pair of rechargeable batteries 40, the central processing unit 42, the tetrahydrocannabinol testing device 44, the testing activation control 64, the printer 74, and the rechargeable battery 94 are in operational communication with each other.

What is claimed is:
1. A detection device for cannabinoid use comprising:
a substantially trapezoidal handheld portable base unit having a convexly curved bottom portion, a linear top edge, a right side, a left side, a front side, and an exterior surface;
a display screen disposed on the front side of the base unit proximal the top edge;
an antimicrobial covering disposed on the exterior surface of the base unit;
a first battery compartment disposed within the base unit;
a pair of rechargeable batteries disposed within the first battery compartment;
a central processing unit disposed within the base unit;
a tetrahydrocannabinol testing device disposed within the base unit;
a testing slot having a front end medially disposed on the bottom portion of the base unit and a back end disposed within the tetrahydrocannabinol testing device;

a plurality of elongated rectangular sterile testing strips, each of the plurality of testing strips slidably and removably disposed within the testing slot;

a testing activation control disposed on the front side of the base unit proximal the bottom portion;

a pair of T-shaped attachment slots comprising a right attachment slot and a left attachment slot, each of the right attachment slot and the left attachment slot disposed within the top edge of the base unit proximal the right side and the left side, respectively;

a universal serial bus port medially disposed within the top edge of the base unit between the right attachment slot and the left attachment slot;

a handheld portable printer having a linear bottom surface, a back surface, a right surface, a left surface, a universal serial bus plug substantially medially disposed on the bottom surface, and a pair of T-shaped attachment extensions comprising a right attachment extension and a left attachment extension, each of the right attachment extension and the left attachment extension disposed on the bottom surface proximal the right surface and the left surface, respectively;

a second battery compartment disposed within the portable printer; and a rechargeable battery disposed within the second battery compartment;

wherein a distance between the right attachment slot and the left attachment slot is equal to a distance between the right attachment extension and the left attachment extension;

wherein each of the right attachment extension, the left attachment extension, and the universal serial bus plug simultaneously removably and slidably engages the right attachment slot, the left attachment slot, and the universal serial bus port, respectively;

wherein the tetrahydrocannabinol testing device is configured to analyze and calculate the presence and amount of tetrahydrocannabinol in a person's bloodstream when one of the plurality of testing strips containing a sample of one of the person's saliva and blood is disposed within the testing slot and the testing activation control is depressed by a user;

wherein the display screen is configured to display the presence and amount of tetrahydrocannabinol in the person's bloodstream as calculated by the tetrahydrocannabinol testing device;

wherein the printer is configured to print a receipt showing the presence and amount of tetrahydrocannabinol in the person's bloodstream as calculated by the tetrahydrocannabinol testing device;

wherein the display screen, the pair of rechargeable batteries, the central processing unit, the tetrahydrocannabinol testing device, the testing activation control, the printer, and the rechargeable battery are in operational communication with each other.

2. The detection device for cannabinoid use of claim 1 wherein the plurality of testing strips is a pair of a plurality of testing strips comprising a first pair and a second pair, wherein each of the plurality of testing strips of the first pair is configured to receive a sample of blood and each of the plurality of testing strips of the second pair is configured to receive a sample of saliva, wherein a length of each of the plurality of testing strips of the first pair is shorter than a length of each of the plurality of testing strips of the second pair.

3. The detection device for cannabinoid use of claim 1 further comprising a pair of substantially rectangular rubberized gripping members comprising a right gripping member and a left gripping member, each of the right gripping member and the left gripping member disposed on the right side of the base unit and the left side of the base unit, respectively.

4. The detection device for cannabinoid use of claim 2 further comprising a pair of substantially rectangular rubberized gripping members comprising a right gripping member and a left gripping member, each of the right gripping member and the left gripping member disposed on the right side of the base unit and the left side of the base unit, respectively.

\* \* \* \* \*